United States Patent
Nilsson et al.

(10) Patent No.: US 8,267,894 B2
(45) Date of Patent: Sep. 18, 2012

(54) SELF-CONTAINED PORTABLE APPARATUS FOR ADMINISTRATION OF A DRUG SOLUTION

(75) Inventors: Martin Nilsson, Hovas (SE); Erik Andreen, Torslanda (SE)

(73) Assignee: Astra Tech AB, Molndal (SE)

( * ) Notice: Subject to any disclaimer, the term of this patent is extended or adjusted under 35 U.S.C. 154(b) by 255 days.

(21) Appl. No.: 12/285,700

(22) Filed: Oct. 10, 2008

(65) Prior Publication Data

US 2009/0099545 A1   Apr. 16, 2009

Related U.S. Application Data

(60) Provisional application No. 60/960,770, filed on Oct. 12, 2007.

(30) Foreign Application Priority Data

Oct. 12, 2007 (EP) ..................................... 07118365

(51) Int. Cl.
*A61M 1/00* (2006.01)
(52) U.S. Cl. ........................................ 604/153; 604/141
(58) Field of Classification Search ................. 604/141, 604/142, 153
See application file for complete search history.

(56) References Cited

U.S. PATENT DOCUMENTS

| | | | |
|---|---|---|---|
| 3,468,308 A * | 9/1969 | Bierman | ....................... 604/141 |
| 3,640,276 A | 2/1972 | Dancy, Jr. | |
| 4,507,116 A | 3/1985 | Leibinsohn | |
| 5,163,909 A * | 11/1992 | Stewart | ......................... 604/140 |
| 5,348,539 A | 9/1994 | Herskowitz | |
| 5,554,123 A * | 9/1996 | Herskowitz | ................... 604/141 |
| 5,954,696 A | 9/1999 | Ryan | |
| 6,382,923 B1 * | 5/2002 | Gray | ............................... 417/53 |

FOREIGN PATENT DOCUMENTS

WO    WO-01/26715 A1    4/2001

* cited by examiner

*Primary Examiner* — Kevin C Sirmons
*Assistant Examiner* — Emily Schmidt
(74) *Attorney, Agent, or Firm* — Birch, Stewart, Kolasch & Birch, LLP

(57) ABSTRACT

A self-contained portable apparatus for administration of a drug solution includes a housing having an enclosure for receiving a flexible pouch containing a drug solution, the output of which is connectable to a conduit for delivering the drug solution to a recipient. A pressurization system is arranged for providing a constant and controllable gas pressure to the housing in order to obtain a controllable delivery of the drug solution. The pressurization system includes a pressure source for delivering positive pressure gas; a pressure accumulation tank connected to the source and the second chamber; a one-way valve arranged between the pressure source and the pressure accumulation tank; and a mechanical pressure regulator arranged between the pressure accumulation tank and the housing. Hereby, an extremely stable and well controllable output pressure and output flow is obtainable.

16 Claims, 5 Drawing Sheets what necessitates cumbersome and tedious cleaning and sterilization of the apparatuses before re-use, and also invokes a risk for contamination of the patient.

Further, it is known from the prior art to produce portable and mechanical administration devices. For example, U.S. Pat. No. 3,460,277 discloses a self-contained portable administration apparatus using CO2 cartridges to obtain a relatively precisely regulated gas flow to displace a medical arranged in a pressure collapsible container. To this end, the pump device comprises a casing comprising a collapsible bladder holding the fluid to be driven (the medical liquid) and a second inflatable bladder to be filled with a driving fluid, whereby expansion of the second bladder causes the medical liquid to be controllably expelled. However, this device is still relatively complicated and expensive to produce, and there is also a problem of obtaining a sufficiently continuously stable and controllable pressure acting of the pressure collapsible container holding the medical liquid. Similar problems are also encountered in the apparatus disclosed in U.S. Pat. No. 5,954,696 and U.S. Pat. No. 4,673,392, which are both related to similar types of administration apparatuses.

Consequently, there is still a need for administration apparatuses which are both capable of providing a sufficiently stable and controllable flow rate, and at the same time are safe and inexpensive to produce and use.

SELF-CONTAINED PORTABLE APPARATUS FOR ADMINISTRATION OF A DRUG SOLUTION

This Nonprovisional application claims priority under 35 U.S.C. §119(e) on U.S. Provisional Application No(s). 60/960,770 filed on Oct. 12, 2007 and under 35 U.S.C. 119(a) to Patent Application No. 07118365.1 filed in the Europe on Oct. 12, 2007 the entire contents of which are hereby incorporated by reference.

FIELD OF THE INVENTION

The present invention relates to a self-contained portable apparatus for administration of a drug solution, and in particular an apparatus which is usable for administration of liquid medicaments to a patient, e.g. for use in post-operative pain relief. The apparatus is arranged to provide a very uniform and controllable flow rate.

BACKGROUND OF THE INVENTION

The administration of medical liquids is largely carried out by gravity-induced hydrostatic pressure infusion of the liquid from a bottle or other container suspended above the recipient an acceptable distance. The liquid empties by gravity at a rate of flow which can be regulated by what is known as a drop-by-drop device which reduces the rate of flow by restriction or compression of the flexible tube carrying the liquid which is to be injected. Although this equipment is used in hospitals, it is however bulky, difficult to move, clumsy and slow to set up. Further, the flow rate is not easily controlled since variations in relative positions of the receiving portion of the patient and the dispensing bottle may occur with time as the patient or bottle may be shifted about.

Moreover, previously available pressure-assisted administration devices are often quite complicated and expensive, and also often lack portability. Further, these known apparatuses are often unable to provide, as well as continuously maintain for a long time, a desired flow rate.

Still further, most known administration devices require that the drug solution is discharged from its original container, i.e. from the prepackaged, disposable, standard medical containers, and into a administration reservoir of the administration apparatus. This is normally a rather tedious and cumbersome task, and also invokes a risk for contamination, since the solution must pass through additional handling steps in the preparation and transfer process, prior to being introduced to a patient.

In many situations, a patient may also require a very slow and continuous introduction of medicament liquid into the patient's system, such as a few milliliters per hour for several hours, or sometimes even a day or more. It is therefore very important that these medicament liquid or pharmaceutical solution doses be administered with a highly accurate introduction rate (flow rate), which is maintained very stable during the entire process.

To this end, many of today's administration apparatuses comprises complex electronic systems. For example, such systems may include complex valve arrangement by which the fluid is introduced into the chamber and withdrawn there from, and controlled by a electronic circuitry which includes pressure sensors and logic circuitry which controls fluid pumps which move the liquid. While relatively compact and accurate, these systems are also highly complex, expensive and requires a great deal of electrical power to operate. Further, these apparatuses are solely intended for multi-time use,

SUMMARY OF THE INVENTION

It is therefore an object of the present invention to provide a self-contained, portable apparatus for administration of a drug solution, which at least alleviates the above-discussed problems of the prior art.

This object is achieved with an administration apparatus according to the appended claims.

According to the invention, there is provided a self-contained portable apparatus for administration of a drug solution, said apparatus comprising:

a housing having an enclosure for receiving a flexible pouch containing a drug solution, wherein said enclosure has a first chamber within said pouch and a second chamber arranged outside said pouch, the chambers being arranged in a pressure-transmitting relation within said enclosure;

an output from said first chamber connectable to a conduit for delivering said drug solution to a recipient; and a pressurization system for providing a constant and controllable gas pressure to said second chamber, wherein a controllable pressure is obtained in said first chamber for a controllable delivery of the drug solution.

Further, the pressurization system comprises:

a pressure source for delivering positive pressure gas;

a pressure accumulation tank connected to said source and to said second chamber, arranged to provide a positive pressure reservoir;

a one-way valve arranged between said pressure source and said pressure accumulation tank, enabling gas to flow solely in the direction from the pressure source to the pressure accumulation tank; and a mechanical pressure regulator arranged between said pressure accumulation tank and said second chamber.

The administration apparatus according to the invention is relatively simple, and can be produced relatively cost-effectively. Hereby, it is possible to provide this administration apparatus as a disposable, for one-time use, and the like, which makes it very safe and secure from a contamination point of view. Further, the inventive pressurization system, involving inter alia an accumulation tank, enables a multitude of various pressure sources to be used, and at the same time the provision of a very stable and controllable system, where the pressure acting on the flexible pouch containing the drug solution in the enclosure of the housing is extremely stable over time, and essentially constant even when the flexible pouch is full or nearly empty. Accordingly, the present invention provides a very stable and constant outgoing pressure for the drug solution. Further, the pressure in the pressurization system may always be kept below 3 bar, which reduces the safety risks of the system, and also reduces the safety requirements of the system. The only exception to this is, possibly, the pressure source, where higher pressures may provided. However, in that case the accumulation tank functions as a buffer to the rest of the system, thereby ensuring adequate safety of the overall system.

The present administration apparatus may be equipped with any type of flexible pouch for holding the drug solution, such as prepackaged, disposable, standard medical containers of flexible materials.

The invention is particularly useful for administration of e.g. pain relieving agents such as anesthetics during post-operation treatment of a patient at a low administration rate during a prolonged time. For example, the apparatus may be arranged to provide an output flow rate of the drug solution in the range 1-200 ml/h, and preferably in the range 1-20 ml/h, and most preferably in the range 4-12 ml/h. Further, the apparatus may be arranged to provide an essentially constant output pressure and output flow rate for at least 1 hour, and preferably for at least 12 hours, and most preferably for at least 24 hours.

The administration apparatus may be used for any type of drug solution, such as liquid medicaments for post-surgery pain relief, such as solutions of ropivakain and other local anesthetics, for instance Narop® and Naropin®, both produced by AstraZeneca. However, the administration apparatus may also be used to deliver intravenous fluids and solutions for a wide variety of medical therapies including chemotherapy, antiviral and antibiotic therapy, and also include intravenous introduction of saline solutions, glucose solutions and various other solutions comprising pharmaceuticals. In e.g. post-surgery use of anesthesia, the drug solution may be administered through a catheter after surgery and after closing of the surgical incision.

The present invention is an entirely mechanical construction, which does not need any electronics or the like for its operation. Further, the apparatus may be made very compact, and thereby portable and self-contained. Still further, the drug solution is at all times maintained separated from the pressurization system, which makes the apparatus very safe, and significantly reduces the risk for contamination of the drug solution, and also makes it possible to use less expensive materials in the pressurization system, since these materials need not be compatible for the drug solution, etc.

Due to the extremely accurate pressure provided by the pressurization system and acting on the flexible pouch holding the drug solution, no flow regulation or the like are in principle needed in the conduit transferring the drug solution to the patient. However, in most cases flow control means may still be advantageous in the conduit system. For example, it may be advantageous to provide a branched conduit system, with one branch providing a continuous drug administration to the patient, and a second branch with a liquid reservoir providing the possibility of bolus doses. Typically, the continuous drug administration can e.g. be 1-20 ml/h, and preferably 2-14 ml/h, and the batch-wise (bolus) dosages can be e.g. 5-30 ml extra every 1-6 hour. Further, since the pressurization system provides an essentially constant pressure on the flexible pouch holding the drug solution, it also becomes possible to control the output liquid flow from the apparatus with great accuracy, and by relatively simple means.

The pressure source is preferably a hand-operated pump. Hereby, the pump may be used to manually fill the accumulation tank with an adequate pressure before starting the drug administration, and may also be used during use, for increasing the pressure in the accumulation tank. Most preferably, the pump comprises an air compression cup which is slideably arranged over the pressure accumulation tank. Hereby, a very compact product is obtainable. However, other alternative pressure sources may also be used for filling the accumulation tank, such as a liquefied gas container, and preferably a liquefied $CO_2$ container, or a container with pressurized air.

The one-way valve ensures that pressurized gas is only transferred in the direction from the pressure source to the accumulation tank, and not in the reverse direction. This makes it possible only to activate the pressure source temporarily or intermittently, such as only initially, before starting the drug administration to the patient, or only when the pressure in the accumulation tank becomes lower than a predetermined threshold value.

The mechanical pressure regulator guarantees that a stable and constant gas pressure is provided from the accumulation tank to the second chamber, and that the pressure in the enclosure is automatically adjusted during the emptying of the flexible pouch holding the drug solution. Such mechanical pressure regulators are per se previously known.

The apparatus is preferably arranged to provide an essentially constant output pressure for the drug solution, said output pressure preferably being in the range 0.1-1.0 bar, and most preferably 0.3-0.6 bar.

The pressure accumulation tank is preferably capable of accumulating a pressure exceeding 1 bar, and preferably exceeding 2 bar. Further, as a safety measure, the pressure accumulation tank is preferably provided with a high-pressure relief valve, arranged to release pressure from the accumulation tank if the pressure exceeds a certain threshold limit, such as a threshold limit of 3 bar. Similarly, the enclosure in the housing may be provided with a high-pressure relief valve, arranged to release pressure from enclosure if the pressure exceeds a certain threshold limit.

The second chamber is preferably arranged as an expandable bladder, said bladder being arranged adjacent to said flexible pouch within said enclosure. However, alternatively, the second chamber may be provided in the enclosure by means of a flexible membrane arranged between a compartment holding the first chamber and a compartment forming the second chamber. Still further, the second chamber may be the entirety of the enclosure being exteriorly from the flexible pouch holding the drug solution, whereby the gas acts directly on the flexible pouch.

The housing is preferably made of relatively rigid material, and preferably a rigid plastic material.

A manometer is preferably arranged on the pressure accumulation tank, for providing an indication of the current pressure in said tank. This can be used for monitoring the present pressure of the tank, and also for monitoring the operation of the drug administration.

Further, the housing is preferably further provided with a manually controllable valve for releasing the pressure of the second chamber. Hereby, the pressure of the second chamber can at all times be released to atmosphere pressure, for e.g. for exchange of the flexible pouch or other maintenance operations.

Still further, the mechanical pressure regulator is preferably arranged between said pressure accumulation tank and said second chamber is controllable to provide different pressures to the second chamber. Hereby, the pressure in the second chamber becomes controllable, and can be set for different pressure levels by means of controlling the pressure regulator. This may e.g. be used for set-up of the administration apparatus for various types of use, or for controlling the pressure of the second chamber during use, for controlling the output flow of the drug solution.

According to another aspect of the invention, there is provided a method for administration of a drug solution, comprising the steps:

providing a flexible pouch containing a drug solution in a housing; and providing a pressure in a second chamber arranged outside said pouch within said housing, said pressure thereby acting on the flexible pouch for delivering said drug solution to a recipient;

wherein said pressure in the second chamber is provided by the additional steps:

providing a positive pressure from a pressure source;

forwarding at least part of said pressure from the pressure source to a pressure accumulation tank connected to said source through in a non-returnable way; and forwarding at least part of said pressure from the pressure accumulation tank to the second chamber through a mechanical pressure regulator arranged between said pressure accumulation tank and said second chamber.

By means of this aspect of the invention, similar advantages are obtainable and corresponding preferred embodiments are feasible as discussed above in relation to the corresponding first aspect of the invention.

These and other aspects of the invention will be apparent from and elicidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein.

DESCRIPTION OF PREFERRED EMBODIMENTS

Figure 1:
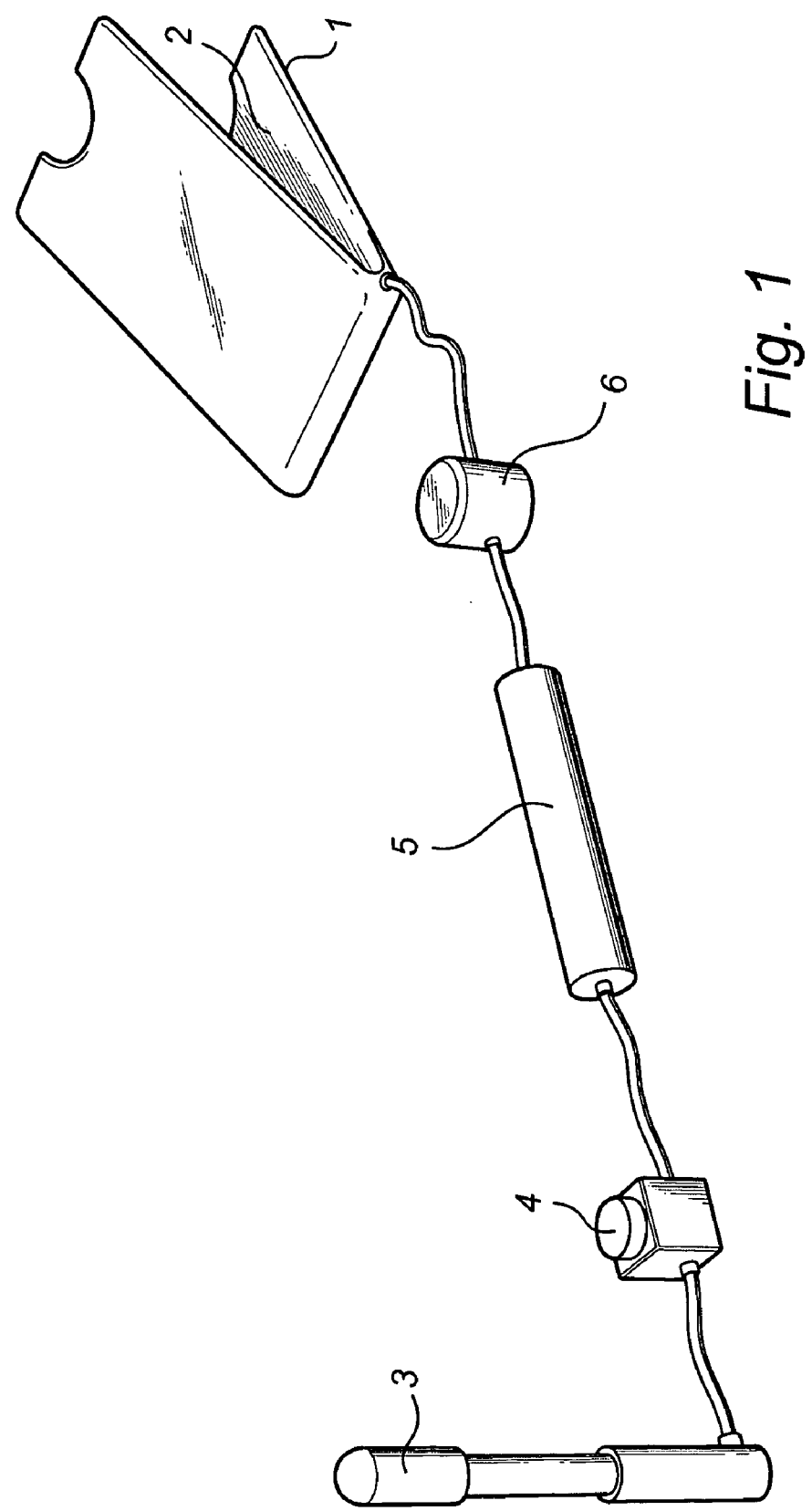
FIG. 1 is a schematic view of the principal construction of an administration apparatus according to a first embodiment of the present invention.

The invention will now be discussed in more detail by means of embodiments. Unless otherwise is specifically mentioned, the different features are mutually exchangeable between the embodiments, and further, the same reference numerals are used to denominate similar or corresponding parts throughout the drawings and the specification.

An administration apparatus for administration of a drug solution according to a basic first embodiment, as illustrated in FIG. 1, comprises a housing 1 having an enclosure 2 for receiving a flexible pouch (not shown) containing a drug solution. In this context "flexible" indicates that the pouch forms a pressure-collapsible container, whereby the liquid arranged in the pouch is releasable by compression operating thereon. The enclosure forms a first chamber within said pouch and a second chamber arranged outside said pouch, wherein the chambers are arranged in a pressure-transmitting relation within said enclosure. Hereby, the pressure provided in the second chamber is transferred to the first chamber, and consequently the pressure provided in the second chamber is essentially equal to the pressure obtained in the drug solution contained in the flexible pouch.

Thus, the housing forms separate chambers for the driving gas and the driven drug solution, formed by separate and abutting collapsible containers, respectively, having a large common interface. The housing forms a rigid container or frame. Part of the housing is formed by a lid or removable wall section, to permit insertion of a new medical container of drug solution, and removal of an emptied container.

The housing is preferably made at least partly of a transparent plastic material in order to permit immediate visual monitoring of the condition of the inner bag. Further, the housing may be injection molded, pressure formed, or the like.

An output from the first chamber is connectable to a conduit (not shown) for delivering said drug solution to a recipient, and in particular to a patient. For example, the conduit may comprise tubing leading from the first chamber, a valve for opening and closing the conduit and a catheter for introduction of the drug solution into the patient. For example, it may be advantageous to provide a branched conduit system, with one branch providing a continuous drug administration to the patient, and a second branch with a reservoir of drug solution providing the possibility of bolus doses. Such conduits are per se known in the art, and will not be discussed in any detail in this application.

Further, the administration apparatus comprises a pressurization system for providing a constant and controllable gas pressure to said second chamber. The pressurization system comprises a pressure source 3 for delivering positive pressure gas. In this embodiment, the pressure source is a hand-actuated pump, but other pressure sources, such as a liquid gas cartridge, are also feasible. A pressurized driving fluid supply meeting these requirements is e.g. a cartridge in which is stored liquefied $CO_2$, fluorocarbons or hydrocarbons contained under pressures required to maintain liquid-gas equilibrium, or gases such as $N_2$ or air under high pressure. Another alternative would be to use an external pressure source, which could then be used for loading the accumulation tank before use of the apparatus, and possible even for subsequent reloading during use.

The pressure source 3 is connected to a pressure accumulation tank 5, which provides a positive pressure reservoir. The accumulation tank is preferably arranged to be pressurized up to a positive pressure during initialization of the administration apparatus, e.g. up to 1-2 bar, or even up to 3 bar. However, it is in many cases an advantage to have an accumulation tank having a pressure below 3 bar connected to the administration system, since this provides lower safety risks, and therefore requires less safety requirements. In many applications, the initial loading of the accumulation tank will be sufficient for the whole administration process. However, it is also possible to reload the accumulation tank during operation. Between the pressure source 3 and the accumulation tank 5 a one-way valve 4 is provided, which allows gas to flow from the pressure source to the accumulation tank, but prevents gas from flowing in the opposite direction.

The accumulation tank is connected to the second chamber within the enclosure 2 via a mechanical pressure regulator 6, arranged to control the pressure within the second chamber to a predetermined pressure level, said pressure level being lower than the pressure of the accumulation tank. The pressure regulator is arranged to mechanically and automatically control the output pressure to a predetermined value. Optionally, this predetermined value may be manually controllable, in order to enable adjustment of the predetermined value during operation, or for adjustment between various types of operations. Thus, the pressure regulator 6 reduces the pressure of the driving fluid from a lever $p_1$ to a level $p_2$, and the latter may be varied within limits by adjustment of a regulator control (not shown). Normally, $p_2$ is much less than $p_1$. The regulator control for adjustment of the output pressure may e.g. adjust a spring tension in the regulator. Several pressure regulators, both of spring and diaphragm type, are per se known in the art, and are commercially available.

Figure 2:
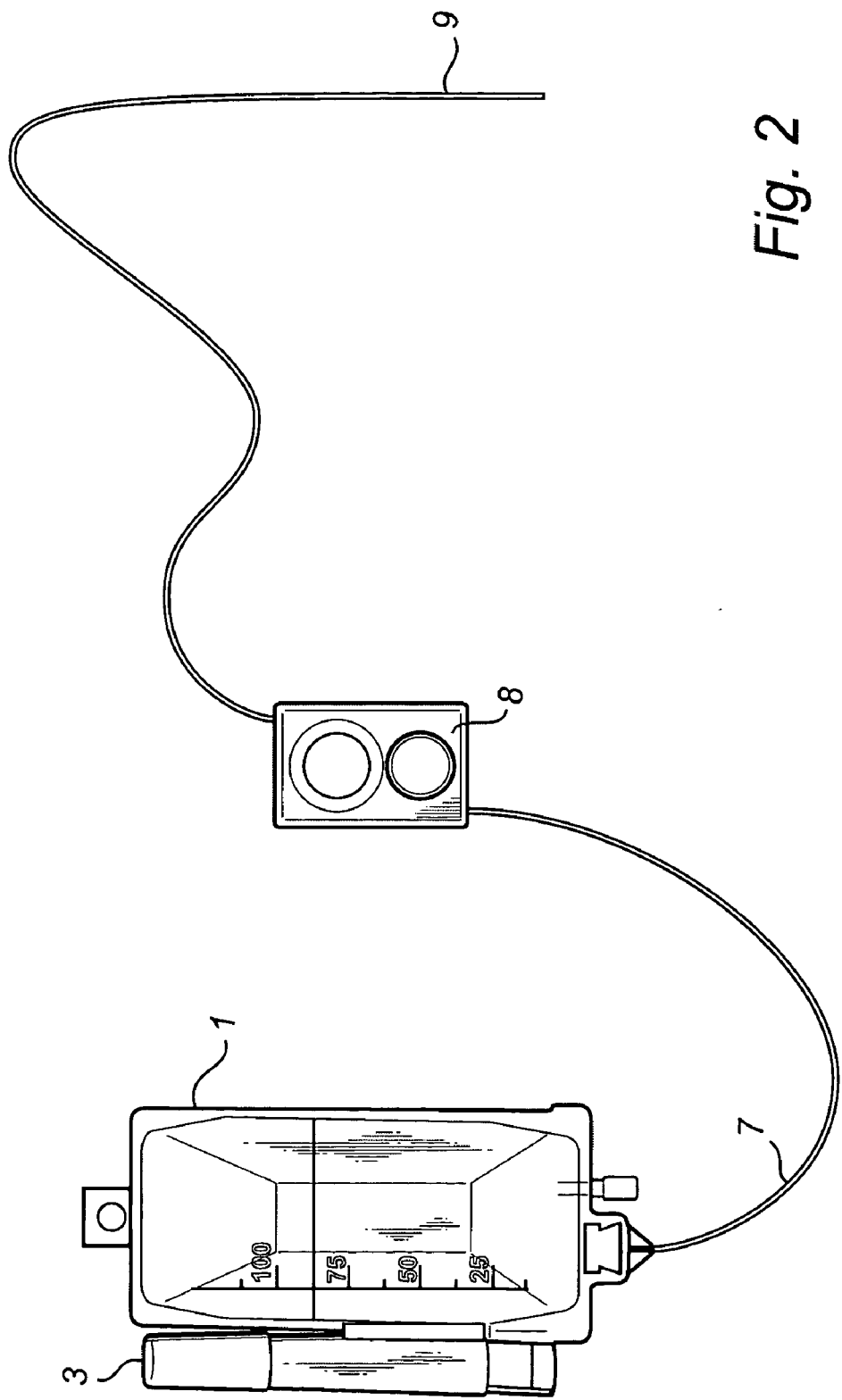
FIG. 2 shows a second embodiment of an administration apparatus according to the present invention.
Figure 3:
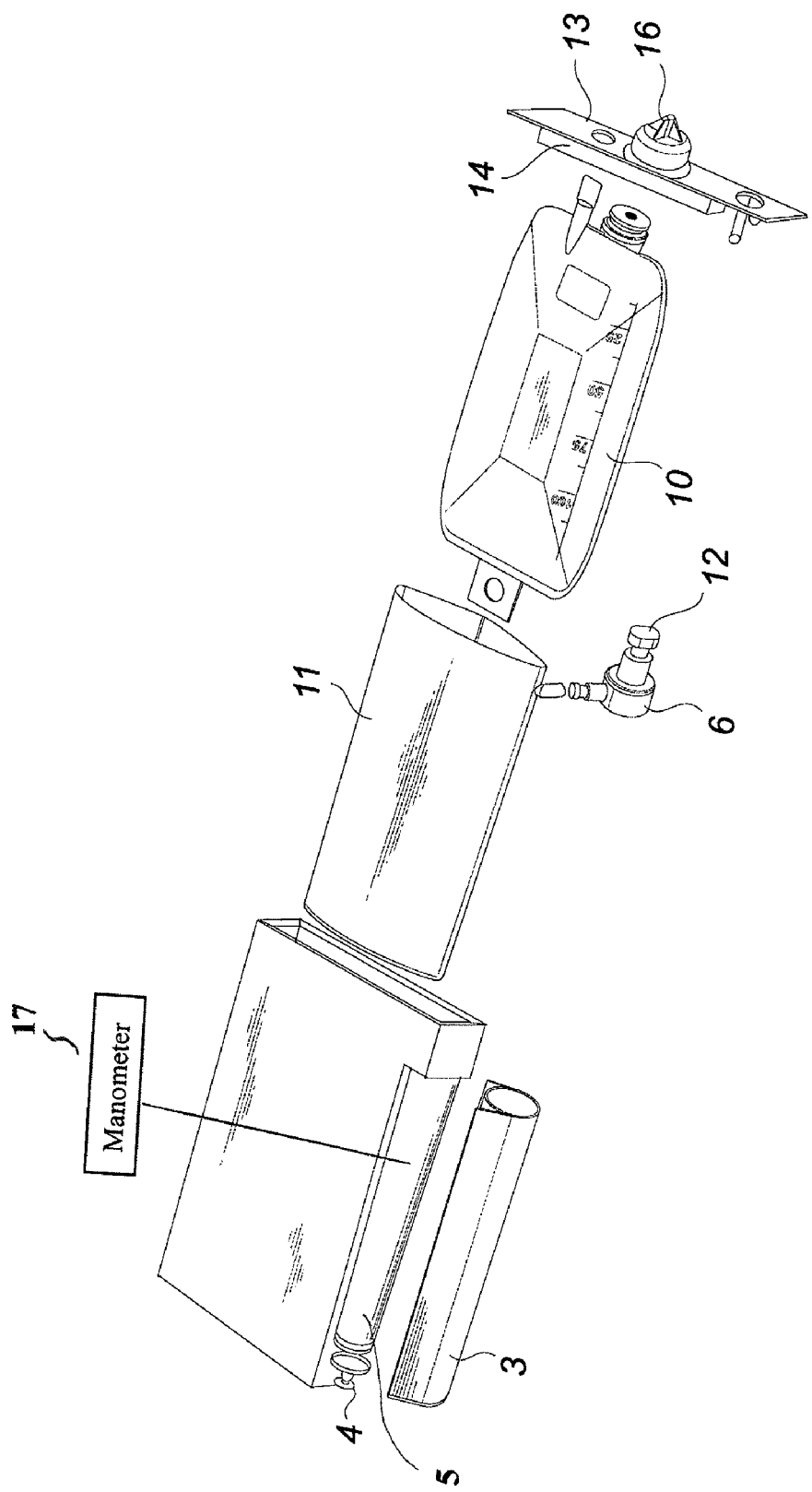
FIG. 3 is an exploded view of the administration apparatus of FIG. 2.

The administration apparatus is preferably arranged as a self-contained and portable device. Even though this goal may be achieved by means of the apparatus discussed above in respect of FIG. 1, the embodiment illustrated in FIGS. 2 and 3 illustrate an even more compact, portable and self-contained apparatus.

The housing 1 receives a flexible pouch 10 for holding the drug solution, such as prepackaged, disposable, standard medical containers of flexible materials, said pouch forming the first chamber. In practice, any one of a number of standard drug solution containers may be used with the administration apparatus of the present invention, but solution containers in the range 50-500 ml are preferred, and most preferably in the rage 100-300 ml.

An inflatable bladder 11 is wrapped around the flexible pouch 10 and also arranged within the housing 1, thereby forming the second chamber.

The housing 1 forms a receptacle with an openable lid 13. After insertion of the flexible pouch 10, the lid 13 is closed. Preferably, the lid is arranged with a snap lock, such as flexible locking arms 15. However, the lid may be attached to the housing bottom by any of a variety of conventional mechanical fasteners, such as push-pins, screws, snap-fit posts and detents, and the like.

Further, the lid is preferably arranged with an inner wall 14 to be inserted into the housing 1. Hereby, the lid stabilizes the housing, and thereby aids in the resistance against the positive pressure building up within the housing during operation. Still further, the lid is preferably arranged with an output opening 16, which is connectable to a conduit (not shown) for delivering said drug solution to a recipient, and in particular to a patient. The conduit for delivering the drug solution to the patient may comprise a needle or other device, such as a catheter, for administering fluids, and tubing connecting the output opening 16 to the needle or catheter end. The conduit may also comprise filters, such as air elimination filters and particle elimination filters, bisections for enabling both bolus doses and continuous administration, flow controlling resistive lumen or orifices etc. Such conduits are per se known in the art.

The output opening may be connected to an internal needle or spike, which penetrates a membrane of the flexible pouch during insertion of the pouch into the housing and closing of the lid. Hereby, fluid connection between the flexible pouch and the administration conduit is obtained automatically during arrangement of the flexible pouch within the housing. The drug spike may be of the type which is per se well known in the art. However, other type of access means are feasible. For example, the output opening may simply be an opening, through which a connection part of the flexible pouch is accessible.

The pressurization system is arranged on the side of the housing, and formed as integrated parts on or within the housing 1. In this embodiment, the accumulation tank 5 is arranged at the side of the housing, and essentially extending over the whole length of the housing. A gap is formed between the accumulation tank and the housing in one end of the tank, so that the accumulation tank is only connected to the housing in one end. Further, the accumulation tank has a uniform cross-section at least in the part not connected to the housing, and preferably an essentially circular cross-section. Further, an opening with a non-return valve 4 is arranged at the end side of the non-connected end of the tank. A hand-actuated pump, functioning as a pressure source 3, is arranged outside the accumulation tank 5, and in particular outside the part of the tank which is not connected to the housing, and is displaceable or slideable in the length direction of the tank. Hereby, the pump forms a cylinder, or a compression cup, with an internal cross-section which generally corresponds to the external cross-section of the corresponding part of the accumulation tank, whereby a relatively tight seal is formed between the pump and the accumulation tank. However, other alternative pressure sources may also be used for filling the accumulation tank, such as a liquefied gas container, and preferably a liquefied $CO_2$ container or a container of pressurized air.

The accumulation tank 5 is connected to the inflatable bladder 11 within the enclosure 2 via a mechanical pressure regulator 6, arranged to control the pressure within the inflatable bladder to a predetermined pressure level, lower than the pressure of the accumulation tank.

During operation, the pump 3 is displaced up and down on the accumulation tank, whereby air is forced through the one-way valve 4 into the accumulation tank 5, whereby a pressure is built up in the tank. This positive pressure is gradually released to the inflatable bladder 11 through the exact control of the regulator 6, whereby a very exact and constant pressure is applied on the liquid medicine arranged in the flexible pouch 10.

The volume of the pressure accumulation tank as well as the initial pressure as provided by the pressure source are preferably selected in dependence of the total volume of the drug to be administered, and the desired output pressure in the second chamber of the housing. Preferably, the volume of the accumulation tank is relatively small, in order to reduce the overall size of the apparatus. For example, it is preferred that the accumulation tank has an internal volume $V_{acc}$ that is less than the internal volume $V_{pouch}$ of the pouch (first chamber) holding the drug solution, and preferably less than 70% of this volume, and most preferably less than 50% of this volume. Further, it is preferred that the pressure source is operable to provide an initial pressure to the accumulation tank that is sufficient to completely empty the pouch. Accordingly, the pressure source is preferably operable to provide a pressure $P_{acc,initial}$ to the accumulation tank that fulfills the following condition:

$$P_{acc,initial} \geq P_{reg} * (V_{acc} + V_{pouch})/V_{acc}$$

where $P_{reg}$ is the regulated pressure of the second chamber, acting on the first chamber (i.e. the pouch), $V_{pouch}$ is the volume of the pouch, i.e. the volume of the drug to be administered, and $V_{acc}$ is the volume of the accumulation tank.

The administration apparatus is particularly useful for administration of e.g. pain relieving agents such as anesthetics during post-operation treatment of a patient at a low administration rate during a prolonged time. For example, the apparatus may be arranged to provide an output flow rate of the drug solution in the range 1-200 ml/h, and preferably in the range 1-20 ml/h, and most preferably in the range 4-12 ml/h. Further, the apparatus may be arranged to provide an essentially constant output pressure and output flow rate for at least 1 hour, and preferably for at least 12 hours, and most preferably for at least 24 hours. Further, an essentially constant output pressure for the drug solution can hereby be provided, e.g. in the range 0.1-1.0 bar, and most preferably 0.3-0.6 bar.

Further, as a safety measure, the pressure accumulation tank is preferably provided with a high-pressure relief valve 12, arranged to release pressure from the accumulation tank if the pressure exceeds a certain threshold limit. Similarly, the enclosure in the housing may be provided with a high-pressure relief valve, arranged to release pressure from enclosure if the pressure exceeds a certain threshold limit. The high-pressure relief valve may also be arranged to provide an alarm sound or the like, such as a whistle tone, when it is activated. Manometers (e.g. 17 in FIG. 3) and the like may also be provided to indicate the present pressure in e.g. the accumulation tank or the second chamber during use. Such a manometer may also be used for monitoring the flow of drug solution out of the administration apparatus, and/or as a measure of the amount of drug solution remaining in the flexible pouch.

Experimental Results

An administration apparatus as discussed above with reference to FIG. 2 was used for experimental measurements. The output of the apparatus was connected to a flow regulator, which allowed a flow of 4 ml/h at an overpressure of 0.4 bar. The output of the flow regulator was forwarded through a catheter, and the drug administered through the catheter was collected and weighed. Further, manometers were used to measure the pressure in the first and second chamber of the housing.

For the experiments, a pouch holding a drug solution was arranged in the housing, and administered by means of the administration apparatus. The weight of the administered drug was continuously measured, together with the pressure in the first and second chamber, until the nominal volume was delivered from the pouch.

Figure 5:
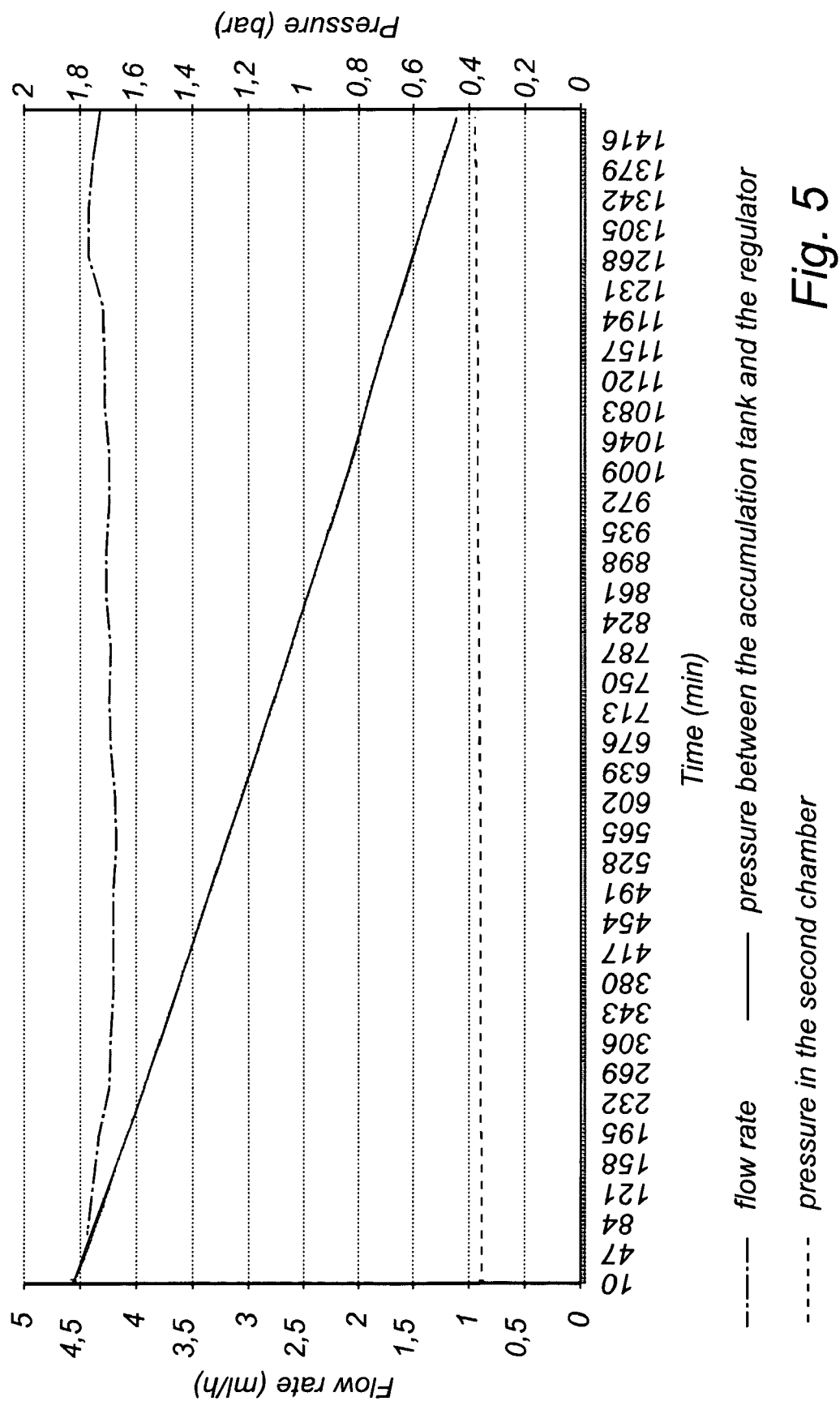
FIG. 5 is a diagram illustrating the measured pressure in the second chamber and the accumulation tank, as well as the resulting flow for the second chamber, of the administration apparatus of FIGS. 2 and 3 during operation.

The result of this measurement is presented in the diagram of FIG. 5. In this diagram, the x-axis represents the time, extending from close to 0 minutes to about 1500 minutes (25 hours), which is the time when the nominal volume was delivered from the pouch. On the y-axis, flow and pressure are represented. FIG. 5 illustrates the pressure in the second chamber (dashed line) and the corresponding pressure in the accumulation tank (full line). Further, the resulting flow rate (dash dotted line) is illustrated. Accordingly, it is clearly discernible how the pressure in the accumulation tank constantly falls from a relatively high pressure level to a pressure level only slightly above the pressure in the second chamber, whereas the pressure in the second chamber, as well as the output flow rate, remain essentially constant and extremely stable during the entire process.

Accordingly, the new drug administration apparatus exhibits a very stable output flow and output pressure, with a very limited variation over the entire process. As a comparison, a similar evaluation was made for some commercially available drug administration apparatuses. The result of this evaluation is presented in the diagram of FIG. 4, in which the x-axis represents the relative amount of delivered drug, extending from 0% of the nominal value to 100% of the nominal volume. The y-axis indicates the deviation in percent at each time from the average flow. The evaluated administration devices were:

the administration apparatus according to the present invention. (Dotted line);

comparative example I is an elastomeric balloon infusion system with a nominal flow rate of 5 ml/h and a nominal volume of 240 ml. (Dashed line);

comparative example II is an elastomeric balloon infusion system with a nominal flow rate of 5 ml/h and a nominal volume of 270 ml. (Full line);

comparative example III is a spring-operated infusion system with a nominal flow rate of 4 ml/h and a maximum volume of 100 ml. (Dash dotted line); and comparative example IV is an elastomeric balloon infusion system with a nominal flow rate of 5 ml/h and a nominal volume of 275 ml. (Dash dotted line with double dots).

Figure 4:
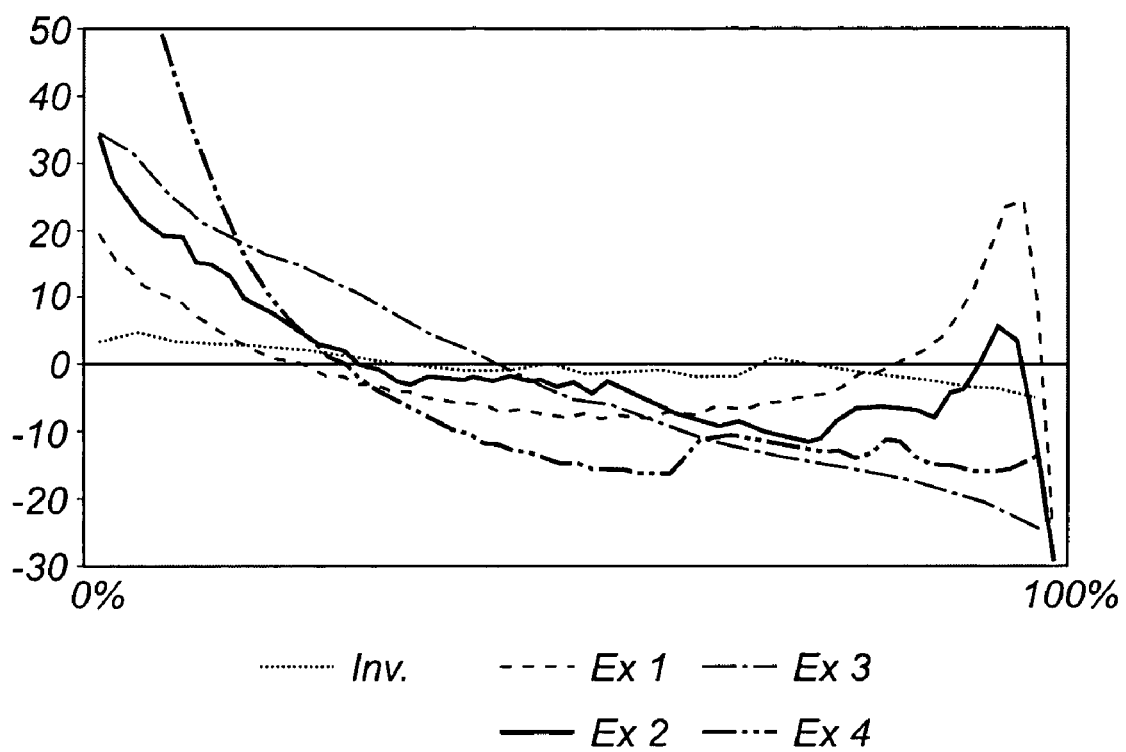
FIG. 4 is a diagram illustrating the deviation in the average output flow over the entire operation cycle for the present invention and a number of comparative examples.

From the evaluation in FIG. 4, it is clearly noticeable that the commercially available comparative examples I-IV all have much higher deviations from the average flow rate during the process, and typically with a flow rate much above the average in the initial phase, when the chamber or pouch containing the drug solution is full, and with a flow rate much below average during the final phase, when the chamber/pouch is almost empty.

CONCLUSION

The drug administration apparatus of the present invention is a self-contained and portable apparatus, which, by reason of its convenience and simplicity of use, is well suited for a large variety of drug administration applications. The apparatus according to the invention does not require any skill in use. It is easily and quickly positioned. It can easily be moved and carried by the injured person or by the medical staff, and thereby causes no hindrance in handling and transporting the patient. The simplicity of the constituent parts also guarantees a low manufacturing cost. Consequently, the apparatus can also be made as a disposable, for use on only one patient. This, in combination with the separation of the pressurization system and the drug and the fact that the drug is allowed to remain in its pre-packed container, provides an extremely clean and secure drug administration, which minimizes the risk for contamination for the patient.

At the same time, the present invention provides, in a medical liquid administration system, means for providing an adequately regulated output pressure from the pressurization system, acting on the drug to be administered, to selectively, reliably, and accurately displace the drug and cause the drug also to flow at a substantially constant flow rate. Hereby, the drug can be allowed to remain in a pre-packed flexible bag during the whole administration process, and with the pressurization system fluidly separated from the drug, and is also usable with standard manufacturers' drug solution containers to provide efficient, accurate and low cost administration.

The administration apparatus of the illustrated embodiment uses a compact, reliable and cost effective pressure source, such as a mechanical, hand-operated pump. The administration apparatus is particularly reliable and cost-effective since it includes neither electronic components to control or monitor operation, nor batteries as a primary power source. Because of its compact construction the administration apparatus according to the invention is able to function even after having been dropped, and because of its lack of electronics, the pump is able to operate even if it comes into contact with water or the like from the outside. Still further, the pumping means can be made very compact, as a cup like member arranged around the accumulation tank. Still further, the present administration apparatus allows easy exchange of the pouch holding the drug.

Specific embodiments of the invention have now been described. However, several alternatives are possible, as would be apparent for someone skilled in the art. For example, the second chamber, providing the external pressure on the first chamber, i.e. the pouch, within the housing may be provided in various ways. One alternative is to arrange the second chamber within a second pouch, or a flexible bag, as discussed above. More than one pouch forming the second chamber may also be provided, such as two flexible bags arranged on each side of the pouch holding the drug solution. Another alternative to make the housing air-tight, whereby the second chamber may be the part of the housing externally from the pouch holding the drug solution.

Further, even though an important application of the present administration apparatus is to administer a drug solution, such as anesthetics, directly to a patient, other applications are also feasible, such as administration of a drug solution to another apparatus or the like. Further, the administration apparatus may be used for a large variety of different drugs, such as for use in open wounds, e.g. for post-surgical treatment, for use during surgery, for intravenous use, for epidural administration, for cancer treatment, neurosurgery, etc. In general, the present administration apparatus is useable for all applications where a pressure is needed for forwarding the drug from the drug container to the place where it is needed.

Still further, the apparatus may be arranged to provide a predetermined output pressure and output flow from the first chamber. Alternatively, the output pressure may be controllable, e.g. by the provision of a controllable pressure regulator between the accumulation tank and the second chamber. Alternatively or additionally, a flow regulator or controllable flow restrictor, such as capillaries of various sizes, may be used for controlling the output flow from the first chamber.

Such and other obvious modifications must be considered to be within the scope of the present invention, as it is defined by the appended claims.

The invention claimed is:

1. A self-contained portable apparatus for administration of a drug solution, said apparatus comprising: a housing having an enclosure for receiving a flexible pouch with a first chamber therein containing a drug solution, wherein said enclosure has a second chamber arranged outside said pouch, the chambers being arranged in a pressure-transmitting relation within said enclosure;
   an output from said first chamber connectable to a conduit for delivering said drug solution to a recipient;
   and a pressurization system for providing a constant and controllable gas pressure to said second chamber, wherein a controllable pressure is obtained in said first chamber for a controllable delivery of the drug solution, wherein said pressurization system comprises:
   a pressure source for delivering positive pressure gas;
   a pressure accumulation tank connected to said pressure source and to said second chamber, arranged to provide a positive pressure reservoir;
   a one-way valve arranged between said pressure source and said pressure accumulation tank, enabling gas to flow solely in the direction from the pressure source to the pressure accumulation tank; and
   a mechanical pressure regulator arranged between said pressure accumulation tank and said second chamber, wherein the pressurization system is integrated on or within the housing, the pressure source comprises a mechanical, hand-operated pump, and the second chamber is formed by an inflatable bladder, said inflatable bladder wrapping around the flexible pouch containing the drug solution,
   wherein the mechanical, hand-operated pump comprises an air compression cup which is slideably arranged over the pressure accumulation tank.

2. The apparatus of claim 1, wherein the drug solution is an anesthetic.

3. The apparatus of claim 1, wherein it is arranged to provide an output flow rate of the drug solution in the range 1-200 ml/h, and preferably in the range 1-20 ml/h, and most preferably in the range 4-12 ml/h.

4. The apparatus of claim 1, wherein it is arranged to provide an essentially constant output flow rate for at least 1 hour, and preferably for at least 12 hours, and most preferably for at least 24 hours.

5. The apparatus of claim 1, wherein it is arranged to provide an essentially constant output pressure for the drug solution, said output pressure preferably being in the range 0.1-1.0 bar, and most preferably 0.3-0.6 bar.

6. The apparatus of claim 1, wherein the pressure accumulation tank is capable of accumulating a pressure exceeding 1 bar, and preferably exceeding 2 bar.

7. The apparatus of claim 1, wherein the pressure accumulation tank is provided with a high-pressure relief valve, arranged to release pressure from the accumulation tank if the pressure exceeds a certain threshold limit.

8. The apparatus of claim 7, wherein the high-pressure relief valve is arranged to maintain a pressure below about 3 bar in the accumulation tank.

9. The apparatus of claim 1, wherein the enclosure in the housing is provided with a high-pressure relief valve, arranged to release pressure from enclosure if the pressure exceeds a certain threshold limit.

10. The apparatus of claim 1, wherein the housing is made of relatively rigid material, and preferably a rigid plastic material.

11. The apparatus of claim 1, wherein the apparatus forms a disposable product for one time use.

12. The apparatus of claim 1, wherein the enclosure of the housing is arranged to receive a pouch of drug solution which is a standard disposable pre-filled medicament container.

13. The apparatus of claim 1, wherein a manometer is arranged on the pressure accumulation tank, for providing an indication of the current pressure in said tank.

14. The apparatus of claim 1, wherein the housing is further provided with a manually controllable valve for releasing the pressure of the second chamber.

15. The apparatus of claim 1, wherein the mechanical pressure regulator arranged between said pressure accumulation tank and said second chamber is controllable to provide different pressures to the second chamber.

16. A method for administration of a drug solution, comprising the steps:
   providing a flexible pouch containing a drug solution in a housing; and
   providing a pressure in a second chamber arranged outside said flexible pouch within said housing, said pressure thereby acting on the flexible pouch for delivering said drug solution to a recipient;
   wherein said pressure in the second chamber is provided by the additional steps:
   providing a positive pressure from a pressure source;

forwarding at least part of said pressure from the pressure source to a pressure accumulation tank connected to said pressure source in a non-returnable way; and forwarding at least part of said pressure from the pressure accumulation tank to the second chamber through a mechanical pressure regulator arranged between said pressure accumulation tank and said second chamber, wherein the pressure source comprises a mechanical, hand-operated pump, said mechanical, hand-operated pump being integrated on or within the housing, and the second chamber is formed by an inflatable bladder, said inflatable bladder wrapping around the flexible pouch containing the drug solution, wherein the mechanical, hand-operated pump comprises an air compression cup which is slideably arranged over the pressure accumulation tank.

* * * * *